US012153109B2

United States Patent
vom Endt et al.

(10) Patent No.: US 12,153,109 B2
(45) Date of Patent: Nov. 26, 2024

(54) GRADIENT COIL ASSEMBLY FOR A MAGNETIC RESONANCE IMAGING DEVICE AND MAGNETIC RESONANCE IMAGING DEVICE

(71) Applicant: Siemens Healthcare GmbH, Erlangen (DE)

(72) Inventors: Axel vom Endt, Erlangen (DE); Jörg Riegler, Fürth (DE); Simon Körber, Hallerndorf (DE)

(73) Assignee: Siemens Healthineers AG, Erlangen (DE)

( * ) Notice: Subject to any disclaimer, the term of this patent is extended or adjusted under 35 U.S.C. 154(b) by 202 days.

(21) Appl. No.: 17/946,367

(22) Filed: Sep. 16, 2022

(65) Prior Publication Data
US 2023/0086830 A1 Mar. 23, 2023

(30) Foreign Application Priority Data
Sep. 17, 2021 (EP) .................................... 21197316

(51) Int. Cl.
*G01R 33/385* (2006.01)
*A61B 5/00* (2006.01)
*A61B 5/055* (2006.01)
*G01R 33/48* (2006.01)

(52) U.S. Cl.
CPC .......... *G01R 33/385* (2013.01); *A61B 5/0035* (2013.01); *A61B 5/055* (2013.01); *A61B 5/704* (2013.01); *G01R 33/4812* (2013.01); *A61B 2562/182* (2013.01)

(58) Field of Classification Search
CPC .............. G01R 33/385; G01R 33/4812; A61B 5/0035; A61B 5/055; A61B 5/704; A61B 2562/182
See application file for complete search history.

(56) References Cited

U.S. PATENT DOCUMENTS

| 5,304,933 A | 4/1994 | Vavrek et al. |
| 5,560,360 A | 10/1996 | Filler et al. |
| 6,351,123 B1 | 2/2002 | Gebhardt |
| 8,838,202 B2 * | 9/2014 | Kruip ................... A61N 5/1049 600/411 |

(Continued)

FOREIGN PATENT DOCUMENTS

| EP | 3327457 A1 | 5/2018 |
| WO | 9429741 A1 | 12/1994 |
| WO | 2018095587 A1 | 5/2018 |

OTHER PUBLICATIONS

Poole M. et al.: "Split Gradient Coils For Simultaneous PET-MRI" Magn Reson Med. Nov. 2009;62(5):1106-11.

(Continued)

*Primary Examiner* — Gregory H Curran
(74) *Attorney, Agent, or Firm* — Banner & Witcoff Ltd.

(57) ABSTRACT

A gradient coil assembly for a magnetic resonance imaging device is disclosed. The gradient coil assembly comprises a cylindrical carrier with conductors forming three gradient coils associated with three orthogonal physical gradient axes. The cylindrical carrier comprises at least two radial through openings at different angular positions. At least one of the conductors runs through at least one area of the carrier located circumferentially between the through openings.

20 Claims, 5 Drawing Sheets

(56) References Cited

U.S. PATENT DOCUMENTS

| | | | |
|---|---|---|---|
| 10,850,127 B2* | 12/2020 | Overweg | A61B 5/055 |
| 2009/0124887 A1 | 5/2009 | Roell et al. | |
| 2012/0150017 A1* | 6/2012 | Yamaya | G01R 33/481 |
| | | | 600/411 |
| 2019/0274649 A1 | 9/2019 | Fahrig et al. | |

OTHER PUBLICATIONS

Sanchez Clemente Cobos: "Head Gradient Coil For MRI With A Window"; Concepts in Magnetic Resonance Part A, vol. 36A, No. 6; 2010.

Fahrig, R. et al. "A Truly Hybrid Interventional MR/X?Ray System: Feasibility Demonstration" J. Magn. Reson. Imaging, 13: 294-300,N. J. (2001).

Poole, M. et al: "Novel Gradient Coils Designed Using A Boundary Element Method", Concepts in Magnetic Resonance Part B: Magnetic Resonance Engineering, Wiley, US, vol. 31B, No. 3; 2007.

* cited by examiner

GRADIENT COIL ASSEMBLY FOR A MAGNETIC RESONANCE IMAGING DEVICE AND MAGNETIC RESONANCE IMAGING DEVICE

CROSS-REFERENCE TO RELATED APPLICATIONS

The present application claims priority to and the benefit of Europe patent application no. EP21197316, filed on Sep. 17, 2021, the contents of which are incorporated herein by reference in its entirety.

TECHNICAL FIELD

The disclosure concerns a gradient coil assembly for a magnetic resonance imaging device, comprising a cylindrical carrier with conductors forming three gradient coils associated with three orthogonal physical gradient axes. The disclosure further concerns a magnetic resonance imaging device having such a gradient coil assembly.

BACKGROUND

Magnetic resonance imaging (MRI) has become an often-used imaging modality, in particular in medicine. MRI requires a main magnetic field of high field strength and high homogeneity. With respect to magnetic field quality, cylindrical magnetic resonance imaging devices are mostly preferred. Such magnetic resonance imaging devices usually comprise an at least essentially cylindrical main magnet assembly, where superconducting main field coils are provided in a vacuum chamber, in particular cooled by helium. The main magnet assembly defines a cylindrical central opening, in which a gradient coil assembly for providing gradient fields, in particular for spatial encoding and, often, a radio frequency coil assembly, for example comprising a body coil, are received. This arrangement may then be covered by cover elements, such that the patient bore remains open for receiving a patient to be imaged. That is, radially outwards from the patient, a radio frequency (RF) coil assembly, a gradient coil assembly, and the main magnet assembly follow each other.

In most known magnetic resonance imaging devices, the patient in the bore is only accessible through the axial openings of the bore. However, for many medical applications, better access to the patient is desired. For example, access to an imaging volume in the patient may be expedient for other imaging modalities, for example x-ray imaging or PET imaging, and/or for therapy, for example radiation therapy.

To provide such access for medical applications to be combined with magnetic resonance imaging, it has been proposed to split at least the gradient coil assembly into two halves, such that, in the area of the field of view of the magnetic resonance imaging device, a free space, which could be used for placement of medical imaging or therapy devices or to allow such devices to access the field of view in the patient, is provided.

In an article by R. Fahrig et al., "A truly hybrid interventional MR/X-ray system: Feasibility demonstration", J Magn Reson Imaging 13 (2001), pages 294-300, the technical issues related to acquisition of x-ray images inside an open MRI system were studied. A flat-panel x-ray detector was placed under the patient bed, a fixed anode x-ray tube overhead with the anode-cathode axis aligned with the main magnetic field and a high frequency x-ray generator. High-quality x-ray and MR images have been acquired without repositioning the object using the hybrid system.

In an article by Poole et al., "Split gradient coils for simultaneous PET-MRI", Magn Reson Med. 62 (2009), pages 1106-11, it was proposed to place the positron emission tomography detection scintillating crystals in an 80 mm gap between two halves of a 1 T split-magnet cryostat. A novel set of gradient and shim coils has been specially designed for the split MRI scanner to include an 110 mm gap from which wires are excluded so as not to interfere with positron detection.

However, split gradient coils result in a number of disadvantages. These include, for example, lower sensitivity and the requirement of torque compensation for the halves, leading to a further reduction in sensitivity and complicating the shielding of the stray field with regard to the main magnet.

SUMMARY

It is an object of the current disclosure to provide an improved design for gradient coil assemblies for magnetic resonance imaging devices, which, on the one hand, provides access for other diagnostic and/or therapeutic modalities and, on the other hand, provides high sensitivity and good shielding.

In a gradient coil assembly as initially described, this object is achieved by the carrier comprising at least two radial through openings at different angular positions, wherein at least one of the conductors runs through at least one area of the carrier located circumferentially between the through openings.

It is an insight of the current disclosure that for many medical applications, e.g. imaging and/or therapeutic modalities, to be combined with magnetic resonance imaging, access over the full 360 degrees azimuthal angle is not required. Instead, access at a finite number of positions, for example two or four orthogonal positions, is sufficient for many medical applications. Hence, a gradient coil assembly is proposed, which provides access to the field of view of the magnetic resonance device at at least two angular positions. The area between these access points, that is, the through openings, still leaves enough room for the usual carrier structure, e.g. the placement of conductors, strongly reducing the effect of the through openings compared with a completely split gradient coil assembly.

In other words, the access for other diagnostic and/or therapeutic modalities, such as for example, x-ray, PET, radiation therapy (LINAC) and the like, is provided by spatially limited through openings, that is, apertures, which act as passages for radiation and/or particles and/or instruments and/or installation location for medical imaging and/or therapy devices. This replaces a circumferential gap between two halves. The areas circumferentially located between the spatially-limited through openings can be used for conductors of the gradient coils to provide a higher sensitivity (mT/m/A) for the gradient coils. Hence, a reduction of gradient coil efficiency and gradient field quality can be reduced to a required minimum. Furthermore, the mechanical stability is improved, since it is no longer necessary to prevent twisting of the halves against each other.

The through openings (apertures) are (e.g. all) located in the same axial plane of the carrier and/or at an axial center of the carrier, e.g. in a central axial plane, where, usually, the field of view (homogeneity volume) of the magnetic resonance device is located. Hence, the through openings provide access to the field of view of the magnetic resonance imaging device.

The carrier can be constructed using known implementations. For instance, conductors (and optionally other layers) may be placed on plates, from which the carrier is then formed by casting a carrier material, e.g. a resin, around this arrangement. Such methods are, in principle, known in the art and do not have to be discussed in detail here.

In embodiments, at least one, e.g. all, of the through openings are located at an angular position of minimal electric current density. That is, the through openings may be positioned in areas where, by design, the number of conductors of the gradient coil would be very low. However, usually if the physical gradient axes are chosen as the axial direction (e.g. the z direction), the vertical direction (e.g. the y direction) and the horizontal direction (e.g. the x-direction), the angular positions of highest conductor density, and thus highest current density, would be at 0 degrees (uppermost vertical position), 90 degrees, 180 degrees, and 270 degrees. On the other hand, these are preferred positions for access of other medical imaging and/or therapy modalities. For example, medical professionals using a bi-plane x-ray system often use x-ray imaging arrangements oriented along the vertical axis (0 degrees) and along the horizontal axis (90 degrees). In this manner, images acquired by a medical imaging device and/or therapy measures provided by a medical therapy device can be easier understood and interpreted by the medical staff. For instance, placement at 0 degrees (vertical direction) and 90 degrees (horizontal direction) are known to the user and are intuitive.

It is noted at this point that also generally at least one pair of through openings, e.g. all adjacent through openings, are provided at an angular distance of 90 degrees. For example, regarding x-ray applications, in this manner two orthogonal x-ray projection images may be acquired.

To place the through openings in an angular section where only few conductors of the gradient coils would be required for a suitable design, as explained above, in embodiments of the disclosure the angular positions of the through openings are located centrally between two physical gradient axes in the axial plane of the through openings. That is, the through openings have centers at 45 degrees to each of the axes, such that, also in this case, adjacent through openings are angularly displaced by 90 degrees. In an embodiment, four through openings may be provided, one in each quadrant formed by the two physical gradient axes in the axial plane of the through openings. This provides a high symmetry advantageous in coil design and may, for example in an x-ray application, be used to place a transmitter and a receiver opposingly.

As already noted, e.g. at least one through opening provides vertical access (e.g. 0 degrees) and at least one through opening provides horizontal access (e.g. 90 degrees). These angular positions match the locations where the transverse physical gradient axes, if chosen as horizontally (e.g. the x direction) and vertically (e.g. the y direction) as usual, comprise the maximal current density such that a disruption at these angular positions would be nearly as disadvantageous as a complete split. To solve this problem, as will be further discussed with regard the magnetic resonance imaging device according to the disclosure, it is proposed to rotate the transverse gradient axes by 45 degrees in the axial planes, such that the through openings are not in an area with maximum current density, but with minimum current density. Together with the third physical gradient axes in the axial direction, such a set of physical gradient axes still forms an orthogonal set of gradients. For magnetic resonance imaging, these physical gradient axes, which run diagonally, can be easily combined to logical gradient axes, which, as usual, run in the horizontal direction (e.g. the x direction) and in the vertical direction (e.g. the y direction). Such reprocessing to logical gradient axes is, for example, known from methods for acquisition of tilted slices.

In embodiments, the gradient coil assembly may further comprise at least one electrical shield, which is usually positioned radially outward from the conductors forming the gradient coils, i.e. towards the main magnet assembly in the magnetic resonance imaging device. In an embodiment, the shield may also extend at least partially (e.g. completely), through at least one of the areas of the carrier located circumferentially between the through openings.

In embodiments, the shield may comprise an active shielding coil arrangement electrically connected to the gradient coils, wherein at least one electrical connection between the shield and the gradient coils runs through at least one of the through openings. That is, the gradient coil assembly comprises two layers of coils: an inner layer providing the gradient coils and an outer layer providing the active shielding coils. The active shielding coils actively counteract the field generation of the gradient coils to the radially outer side, as is generally known. The presence of the through openings can now be used to further increase the efficiency of the gradient coil assembly. In this embodiment, the through openings are additionally used to directly contact the primary layer (gradient coils) to the secondary (shielding) layer (active shielding coils). In this manner, the inductance of the gradient coil is advantageously reduced such that the efficiency of a gradient coil assembly with through openings is only slightly less than the efficiency of a conventional gradient coil assembly having no through opening.

As one example, as is generally known, the course of the conductors (e.g. also for the electrical shield) may be determined computationally by an optimization algorithm running on at least one processor. Hence, the conductors may be arranged on the carrier according to a pattern generated using the presence of the through openings as a boundary condition, e.g. also providing an interlayer connection surface. That is, the surfaces of the walls emitting the through openings may be included as an interlayer connection surface where conductors connecting the gradient coils and the active shielding coils run. In this manner, the presence of the through openings can optimally be exploited by way of design, providing a highly efficient, low inductance gradient coil assembly comparable in performance to a gradient coil assembly having no access options for further medical applications.

Regarding the dimensions of the through openings, these may be selected corresponding to a field of view of a medical imaging device using the through openings, for example an x-ray imaging device. For example, if a cone-beam geometry is used for x-ray imaging, the dimensions of the through openings may be selected to accommodate the cone-beam emitted from an x-ray source emitting its x-rays through at least one of the through openings. The through opening provides enough space to accommodate the x-ray radiation field. In the example of a radiation therapy device, for example, a particle or photon beam-sized through opening may be provided.

Generally speaking, the through openings may, for example, extend over any suitable angular interval (e.g. of 5 to 15 degrees) in the circumferential direction, such that only a minor part of the full angular interval is used for these apertures.

The disclosure further concerns a magnetic resonance imaging device, comprising a gradient coil assembly according to the disclosure and a main magnet assembly having openings aligned with the through openings of the carrier, wherein at least one medical imaging and/or therapy device is at the last partly received in at least one set of aligned openings. All features and remarks regarding the gradient coil assembly analogously apply to the magnetic resonance imaging device, such that the same advantages can be achieved.

In most cases, the through openings are used for providing access to the field of view of the magnetic resonance imaging device, that is, the homogeneity volume, for example for radiation, particles, and/or instruments. The corresponding medical imaging and/or therapy devices, in most cases, may be placed radially outside the gradient coil assemblies, for example in corresponding openings in the main magnet assembly. However, in some cases, these may also be at least partly placed in the through openings. Generally speaking, the openings in the main magnet assembly do not have to be complete through openings and/or may have different dimensions from the through holes, for example be larger depending on the additional medical application to be implemented.

In embodiments, the magnetic resonance imaging device may further comprise a cylindrical radio frequency coil assembly inside the carrier, which also has through openings aligned with the through openings of the carrier. As already explained, such a radio frequency coil assembly may, for example, comprise a body coil for sending radio frequency pulses and/or receiving magnetic resonance signals. If the medical imaging and/or therapy device uses radiation and/or particles able to pass through the materials of such a radio frequency coil assembly, through openings may, in other embodiments, also not be necessary.

In embodiments, the magnetic resonance imaging device may further comprise a patient table, wherein at least the gradient coil assembly is rotatable around the patient table. Preferably, the main magnet assembly and the gradient coil assembly, e.g. also the radio frequency coil assembly, may be rotatable together around the patient table. If at least the gradient coil assembly is rotatable around the axial direction, a more flexible geometry may be realized. For example, if magnetic resonance imaging and the additional modality provided by the at least one medical imaging and/or therapy device are to be applied successively in time, the gradient coil assembly may be used in a basic position for the additional modality, and in a position rotated 45 degrees for magnetic resonance imaging, such that the physical gradient axes comprise a vertical and a horizontal axis.

As already discussed regarding the gradient coil assembly, the through openings of the gradient coil assembly may e.g. be positioned at a relative angular position of 45 degrees to the respective physical gradient axes. Here, the influence on the efficiency of the gradient coils is reduced. Since, however, the most intuitive positioning for through openings and thus the additional imaging and/or therapy modality to be combined with magnetic resonance imaging are the horizontal and vertical directions (90 degrees and 0 degrees), the physical gradient axes may advantageously run diagonally.

In such a configuration, in an embodiment, the magnetic resonance imaging device may further comprise a control device, wherein the two physical gradient axes perpendicular to the longitudinal axis (e.g. the axial or z direction) are at angles of 45 degrees each to the horizontal and the vertical direction (e.g. the x and y direction), where the openings align, and the control device is configured to process acquired magnetic resonance data to a logical vertical and a logical horizontal gradient axis.

BRIEF DESCRIPTION OF THE DRAWINGS

Other objects and features of the present disclosure will become apparent from the following detailed description considered in conjunction with the accompanying drawings. The drawings, however, are only principle sketches designed solely for the purpose of illustration and do not limit the disclosure. The drawings show.

DETAILED DESCRIPTION OF THE DISCLOSURE

Figure 1:
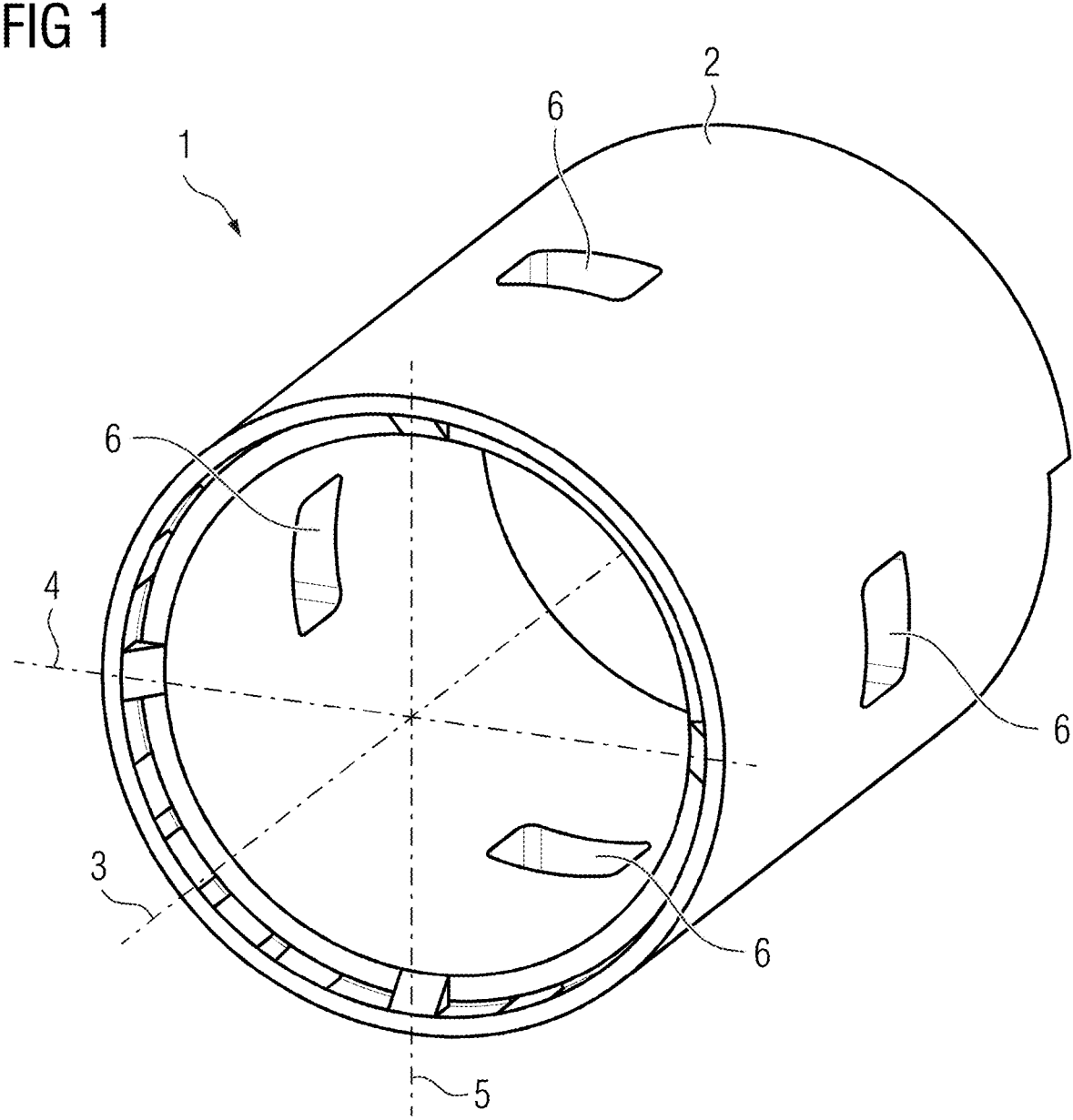
FIG. 1 illustrates an exemplary perspective view of a gradient coil assembly according to one or more embodiments of the disclosure.

FIG. 1 illustrates an exemplary perspective view of a gradient coil assembly according to one or more embodiments of the disclosure. FIG. 1 shows a perspective view of a gradient coil assembly 1 according to the disclosure. As can be seen, the gradient coil assembly 1 comprises a cylindrical carrier 2 extending in an axial direction 3 along a respective longitudinal axis. Additionally, a horizontal direction 4 and a vertical direction 5 are shown. In magnetic resonance imaging devices, the longitudinal axis 3 usually is a z direction, i.e. the horizontal direction 4 is the x direction, and the vertical direction 5 is the y direction. In FIG. 1 and the following Figures, the gradient coil assembly 1 is shown in an orientation in which it is inserted into an aperture of a main magnet assembly of a magnetic resonance imaging device. Here, the vertical upwards direction corresponds to 0 degrees, and a horizontal sidewards direction to 90 degrees. In a central axial plane comprising the homogeneity volume, and thus the field of view of the magnetic resonance imaging device, through openings 6 are provided at 0 degrees, 90 degrees, 180 degrees, and 270 degrees, which are thus angularly spaced apart by 90 degrees each. These through openings 6 (apertures) are provided as access points for an additional diagnostic or therapeutic modality, that is, an additional medical application, for example x-ray imaging, radiation therapy or PET imaging.

Their dimensions are chosen sufficiently for the respective additional modality to be combined with magnetic resonance imaging, e.g. for simultaneous use. For example, if x-ray imaging is used, where, for example, an x-ray source may be placed in a correspondingly aligned opening of the main magnet assembly, the x-ray radiation field dimensions, for example a cone-beam, may define the dimensions of the through openings 6. While, in this example, the x-ray detector may be placed in or behind the opposing through openings 6, the x-ray detector may also be placed inside the bore of the magnetic resonance imaging device, adjacent to the patient, while the opposing through openings 6 serve to provide symmetry advantageous for the design and efficiency of the gradient coil assembly 1, as further discussed below. Generally, however, choosing the horizontal direction 4 and the vertical direction 5 for the additional diagnostic and/or therapeutic modality provides for intuitive use by medical staff.

Figure 2:
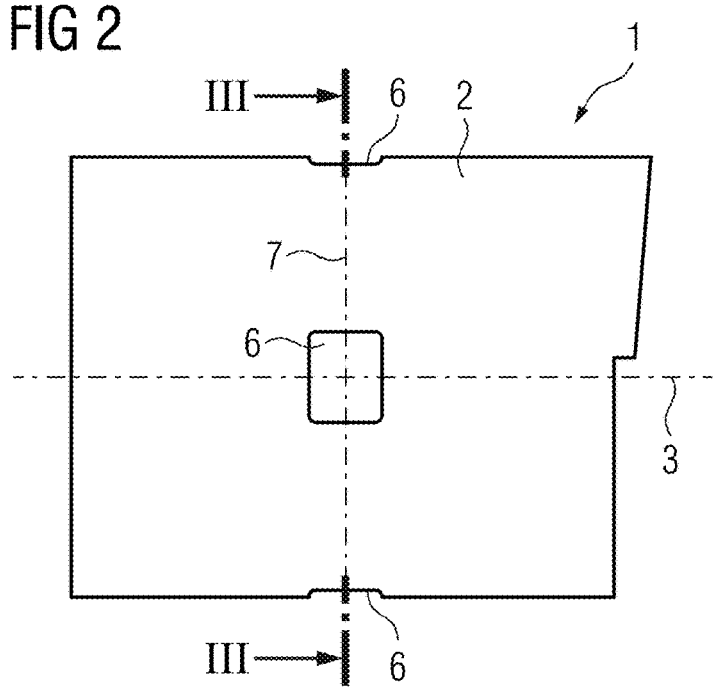
FIG. 2 illustrates an exemplary side view of the gradient coil assembly of FIG. 1, according to one or more embodiments of the disclosure.
Figure 3:
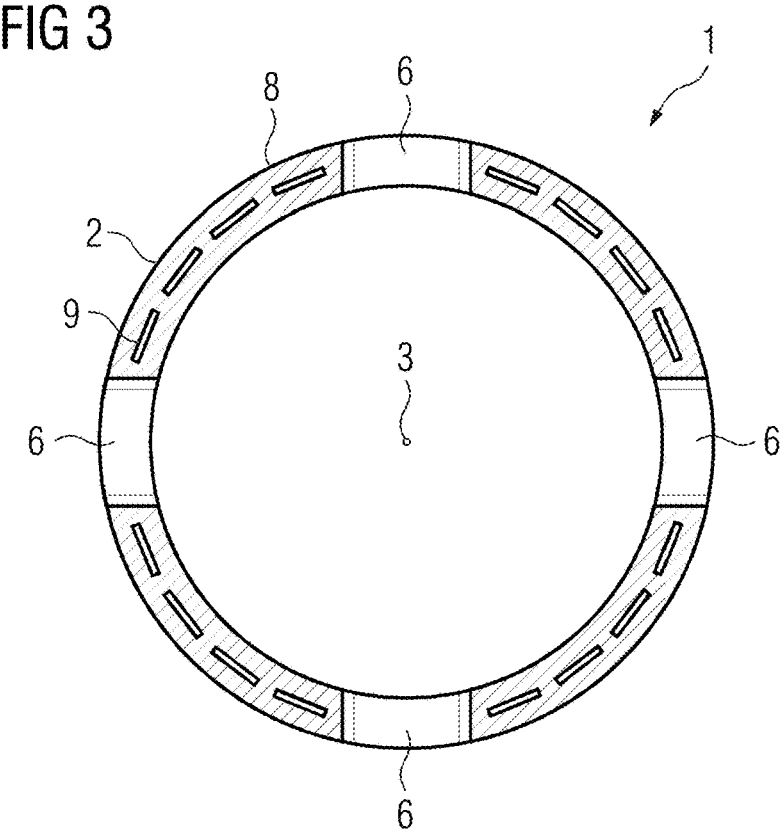
FIG. 3 illustrates an exemplary schematic section view along the line III-III in FIG. 2, according to one or more embodiments of the disclosure.

As can be seen in the cross-sectional view through the central axial plane 7 indicated in FIG. 2, the carrier 2 comprises at least one carrier material 8, and conductors 9 are coarsely indicated in FIG. 3 for ease of explanation.

Figure 4:
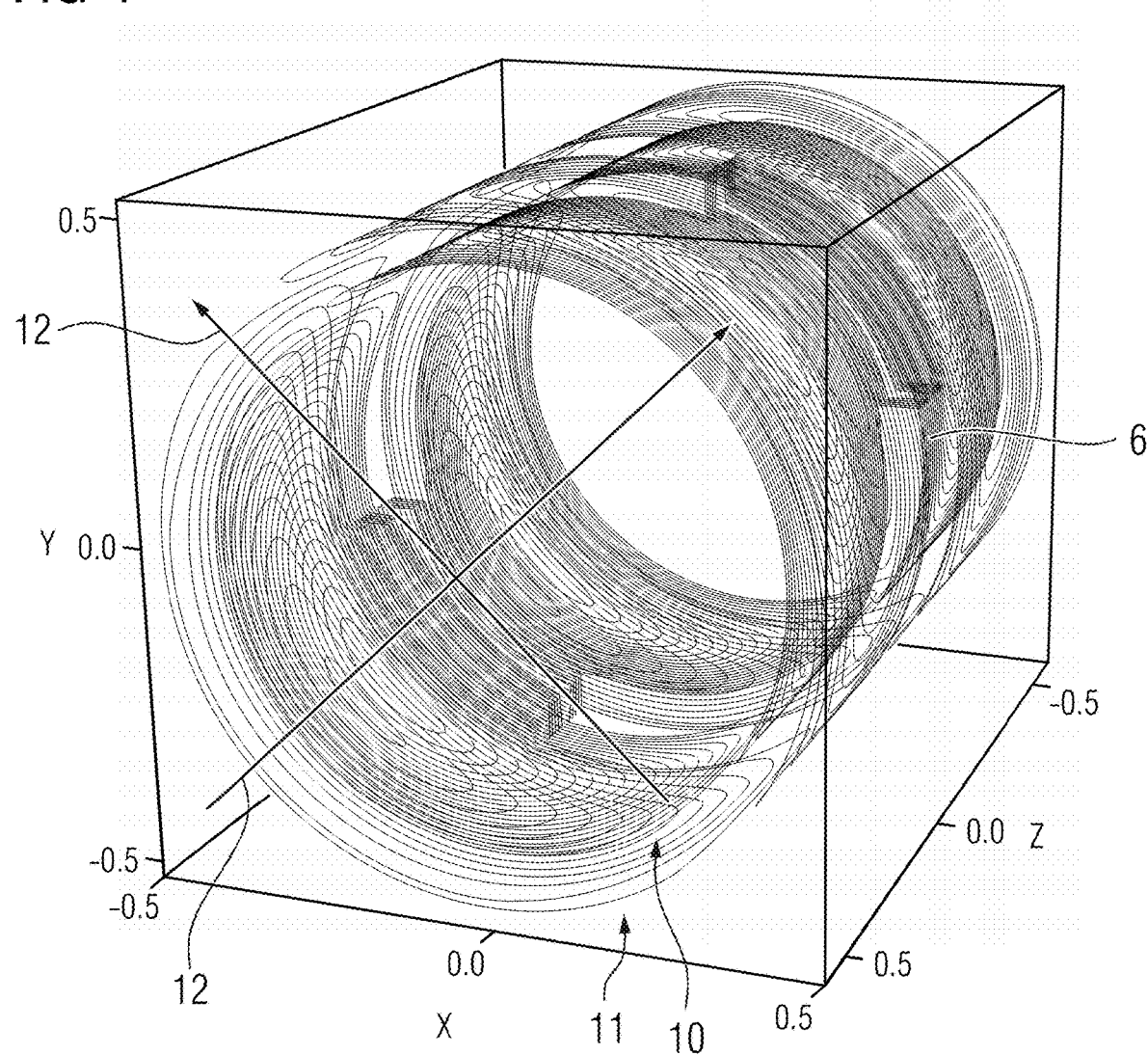
FIG. 4 illustrates an exemplary conductor pattern of the gradient coil assembly of FIG. 1, according to one or more embodiments of the disclosure.

An exemplary conductor configuration and pattern is shown in FIG. 4, where it can be seen that the conductors 9 are arranged in two layers, namely an inner layer 10 and an outer layer 11. Conductors of the inner layer 10 form the gradient coils for three physical gradient axes provided by the gradient coil assembly 1. In this embodiment, the physical gradient axes 12 perpendicular to the longitudinal direction 3 have been rotated from their usual orientation along the horizontal direction 4 and the vertical direction 5 by 45 degrees, and hence run diagonally. This is due to the positioning of the through openings 6, as explained with respect to FIGS. 5 and 6.

Figure 5:
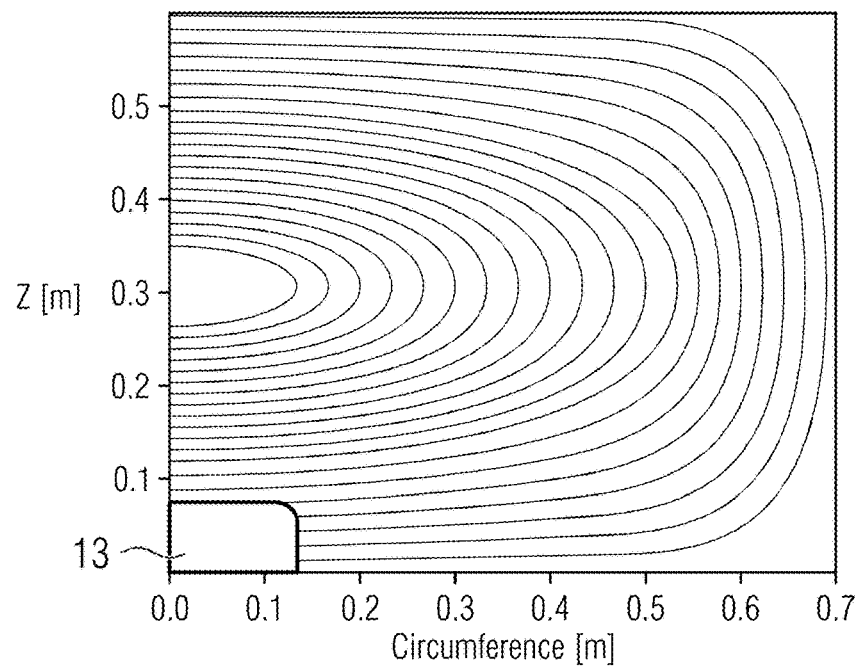
FIG. 5 illustrates a conventional first rolled out depiction of an octant of a transverse gradient layer.

FIG. 5 shows a conventional conductor pattern of a transverse gradient coil in one octant rolled out on the plane spanned by the longitudinal direction 3 and the circumferential direction. If, a through opening, as indicated by box 13, is positioned to provide access in a vertical or horizontal direction, the through opening would thus be positioned in an area of very high conductor density and thus current density, in particular maximum current density, such that the efficiency of the gradient coil would be strongly reduced by placing a through opening 6 here.

Figure 6:
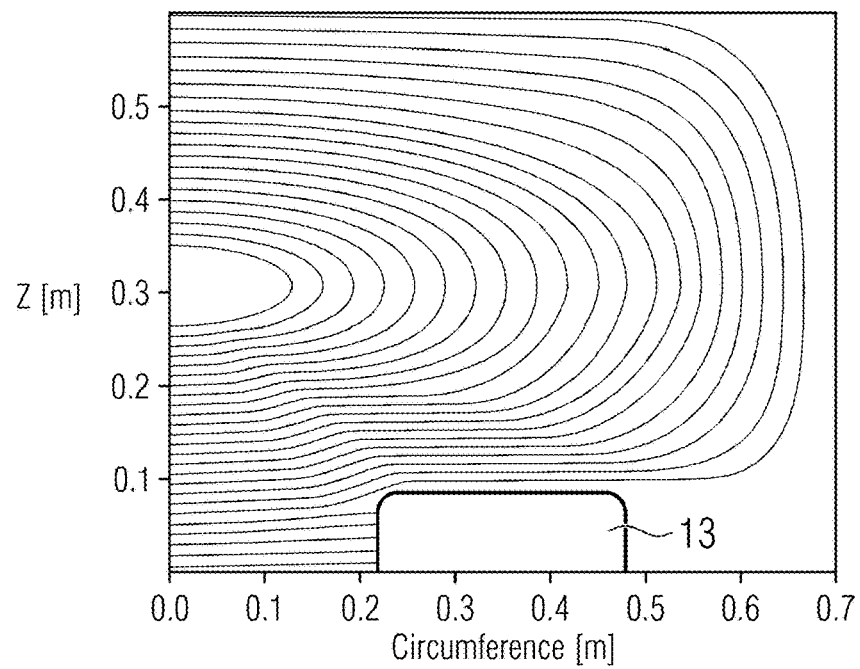
FIG. 6 illustrates an exemplary conductor pattern modified from that shown in FIG. 5, with rotated physical gradient axes, according to one or more embodiments of the disclosure.

However, if the angular positions of the through openings 6 are rotated 45 degrees against the physical gradient axis 12, a position of low current density, in particular minimum current density, is reached, and the conductor pattern can, as shown in FIG. 6, be designed to maintain a high efficiency of the gradient coils and hence the complete gradient coil assembly 1. It is noted that the conductor patterns of FIG. 5 and FIG. 6 only show one gradient coil, while the transverse gradient coil for the perpendicular transverse gradient axis 12 would have its current density maximum at an angular distance of 90 degrees, that is, the right edge of the octant shown in FIGS. 5 and 6, such that the angular position of 45 degrees is the one with minimum current density if all gradient coils are taken into account.

In the magnetic resonance imaging device, a control device may be configured to process acquired magnetic resonance data to use logical gradient axes in the horizontal and vertical directions 4, 5 instead of the tilted physical gradient axes 12.

The conductors of the outer layer 11 form active shielding coils, that is, the outer layer 11 represents an electrical shield of the gradient coil assembly 1. These active shielding coils actively counteract the electromagnetic fields of the gradient coils in the inner layer 10 in the radially outward direction, that is, to the main magnet unit, in accordance with known principles.

The active shielding coils and the gradient coils may be electrically connected, e.g. to reduce the inductance of the gradient coil assembly. In this embodiment, the presence of the through openings 6 is used to provide additional electrical contacting options, e.g. an additional surface for conductors 9 electrically connecting the layers 10, 11, as can be seen in FIG. 4 for the leftmost through opening 6. In other words, the primary layer 10 and the secondary (shielding) layer 11, e.g. gradient coils and active shielding coils associated with respective physical gradient axes 12 are directly electrically connected via the through openings 6, e.g. their wall surfaces as interlayer connection surfaces. In this manner, the inductance of the gradient coils is reduced, increasing the efficiency of the gradient coil assembly 1.

It is noted that the presence of the through openings 6, and hence the interlayer connection surfaces, may also be taken into account when designing the conductor pattern for the gradient coil assembly 1.

Figure 7:
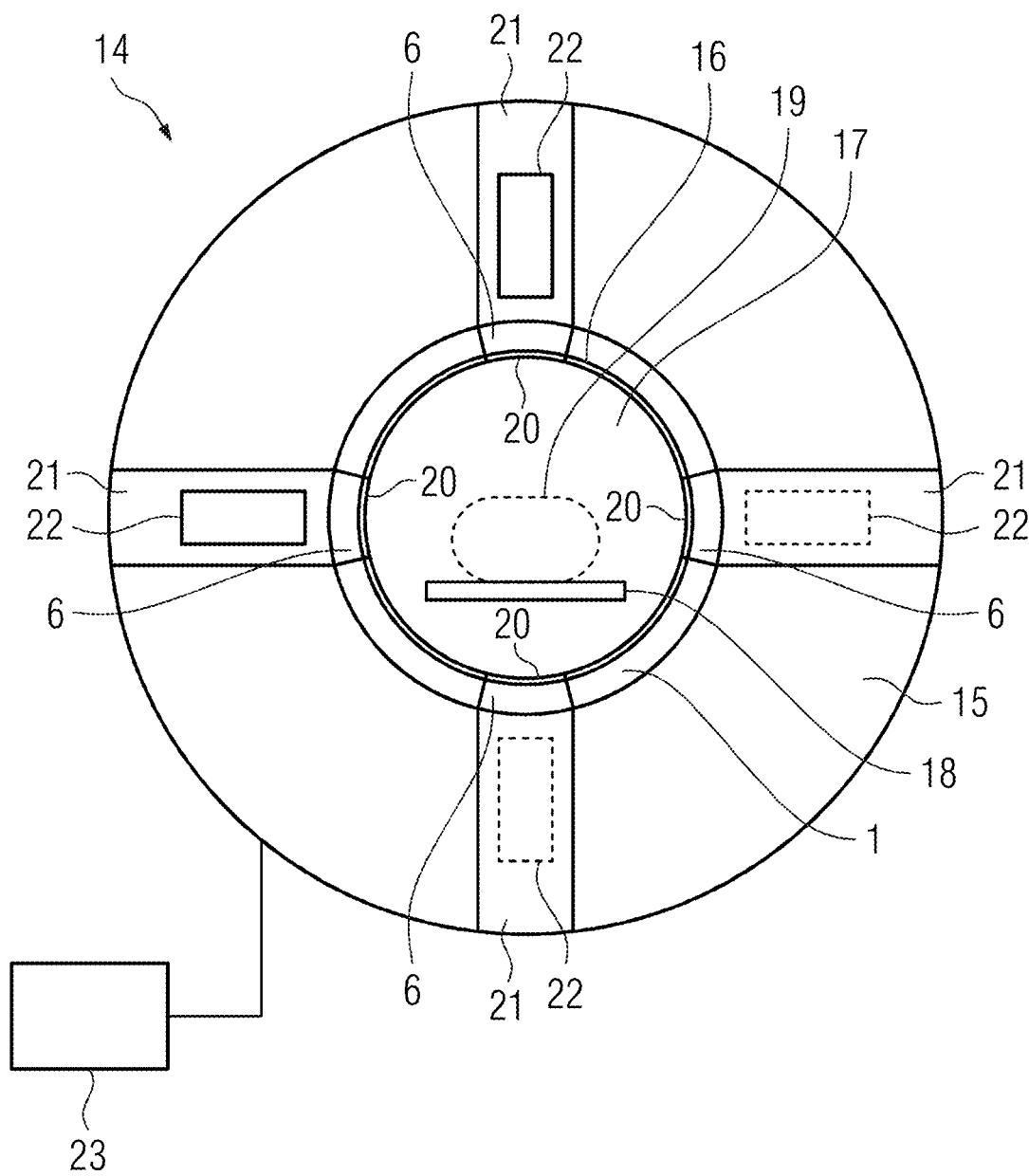
FIG. 7 illustrates an exemplary principle view of a magnetic resonance imaging device, according to one or more embodiments of the disclosure.

FIG. 7 shows an exemplary schematic cross-sectional view of a magnetic resonance imaging device 14 according the disclosure. The magnetic resonance imaging device 14 comprises a radially outer, at least predominantly cylindrical main magnet assembly 15, in which a gradient coil assembly 1 according to the disclosure and an optional radio frequency (RF) coil assembly 16 are received, leaving an open area forming the patient bore 17. Using a patient table 18, an imaging region of the patient can be positioned in the schematically indicated homogeneity volume 19, that is, the field of view of the magnetic resonance imaging device 14.

The RF coil assembly 16 comprises through openings 20 aligned with the through openings 6 of the gradient coil assembly 1. Furthermore, the main magnet assembly 15 comprises openings 21, which do not have to be through openings, aligned with through openings 6 and 20. In the embodiment shown here, medical imaging and/or therapy devices 22 for the additional diagnostic and/or therapeutic modality to be combined with magnetic resonance imaging, for example x-ray imaging components like an x-ray source, are mounted in at least two of the openings 21, allowing access to the homogeneity volume 19 from vertical direction 5 and from horizontal direction 4. In other embodiments, medical imaging and/or therapy devices 22 may also be at least partly received in through openings 6 and/or 20. In the embodiment shown in FIG. 7, radiation and/or particles and/or instruments by the medical imaging and/or therapy devices 22 may pass through the through openings 6 and 20 towards or from the homogeneity volume 19.

Since, as explained with respect to FIG. 4, the physical gradient axes 12 run diagonally, that is at 45 degrees to the vertical direction 5 and the horizontal direction 4, a control device 23 of the magnetic resonance imaging device 14 is configured to process magnetic resonance data from these physical gradient axis 12 to logical gradient axes in the horizontal and vertical directions 4, 5.

Although the present disclosure has been described in detail with reference to the preferred embodiments, the present disclosure is not limited by the disclosed examples from which the skilled person is able to derive other variations without departing from the scope of the disclosure.

The various components described herein may be referred to as "devices" or "units." Such components may be implemented via any suitable combination of hardware and/or software components as applicable and/or known to achieve the intended respective functionality. This may include mechanical and/or electrical components, processors, processing circuitry, or other suitable hardware components configured to execute instructions or computer programs that are stored on a suitable computer readable medium. Regardless of the particular implementation, such devices and units, as applicable and relevant, may alternatively be referred to herein as "circuitry," "processors," or "processing circuitry."

What is claimed is:

1. A gradient coil assembly for a magnetic resonance imaging device, comprising:
a cylindrical carrier; and
a set of conductors forming three gradient coils, the set of conductors being included in the cylindrical carrier, and each one of the three gradient coils being associated with a respective one of three orthogonal physical gradient axes,
wherein the cylindrical carrier comprises two radial through openings disposed at different angular positions with respect to one another,
wherein a conductor from among the set of conductors passes through an area of the cylindrical carrier that is located circumferentially between the two radial through openings, and
wherein the dimensions of the two radial through openings correspond to a field of view of a medical imaging device using the two radial through openings.

2. The gradient coil assembly according to claim 1, wherein one of the two radial through openings is located at an angular position of minimal electric current density.

3. The gradient coil assembly according to claim 2, wherein each one of the two radial through openings is located at an angular position of minimal electric current density.

4. The gradient coil assembly according to claim 1, wherein the two radial through openings are disposed at an angular position of 90 degrees with respect to one another.

5. The gradient coil assembly according to claim 4, wherein the two radial through openings are from among a plurality of radial through openings, and
wherein each adjacent pair of radial through openings from among plurality of radial through openings are disposed at an angular position of 90 degrees with respect to one another.

6. The gradient coil assembly according to claim 1, wherein an angular position of each one of the two radial through openings is centrally located between two physical gradient axes from among the three orthogonal physical gradient axes in an axial plane containing the two radial through openings.

7. The gradient coil assembly according to claim 6, wherein the two radial through openings are from among four radial through openings, and
wherein each one of the four radial through openings is disposed in a respective quadrant formed by the two physical gradient axes of the axial plane containing the two radial through openings.

8. The gradient coil assembly according to claim 1, further comprising:
an electrical shield.

9. The gradient coil assembly according to claim 8, wherein the electrical shield comprises an active shielding coil arrangement electrically connected to the three gradient coils.

10. The gradient coil assembly according to claim 9, wherein the set of conductors are arranged on the cylindrical carrier according to a pattern that is generated using a presence of the two radial through openings as a boundary condition.

11. The gradient coil assembly according to claim 10, wherein the set of conductors are arranged on the cylindrical carrier according to the pattern that is generated by further defining surfaces of walls associated with the two radial through openings as an interlayer connection surface in which the set of conductors connecting each one of the three gradient coils and active shielding coils of the active shielding coil arrangement pass through.

12. The gradient coil assembly according to claim 9, wherein a connection between the electrical shield and each one of the three gradient coils runs through one of the two radial through openings.

13. The gradient coil assembly according to claim 1, wherein the two radial through openings extend over an angular interval having a range between 5 to 15 degrees in a circumferential direction.

14. A magnetic resonance imaging device, comprising:
a gradient coil assembly, comprising:
a cylindrical carrier; and
a set of conductors forming three gradient coils, the set of conductors being included in the cylindrical carrier, and each one of the three gradient coils being associated with a respective one of three orthogonal physical gradient axes,
wherein the cylindrical carrier comprises two radial through openings disposed at different angular positions with respect to one another, and
wherein a conductor from among the set of conductors passes through an area of the cylindrical carrier that is located circumferentially between the two radial through openings; and
a main magnet assembly having a set of openings, each opening from among the set of openings being aligned with a respective one of the two radial through openings of the cylindrical carrier, and
wherein a medical imaging device and/or therapy device is at least partly received in the set of openings.

15. The magnetic resonance imaging device according to claim 14, further comprising:
a cylindrical radio frequency (RF) coil assembly disposed inside the cylindrical carrier,
wherein the cylindrical RF coil assembly has two through openings respectively aligned with the two radial through openings of the cylindrical carrier.

16. The magnetic resonance imaging device according to claim 14, wherein the medical imaging device comprises an x-ray device for simultaneous acquisition of x-ray imaging data and magnetic resonance imaging data.

17. The magnetic resonance imaging device according to claim 14, further comprising:
a patient table,
wherein the gradient coil assembly is rotatable around the patient table.

18. The magnetic resonance imaging device according to claim 17, wherein the main magnet assembly and the gradient coil assembly are each rotatable together around the patient table.

19. The magnetic resonance imaging device according to claim 17, wherein the main magnet assembly, the gradient coil assembly, and the cylindrical RF coil assembly are each rotatable around the patient table.

20. The magnetic resonance imaging device according to claim 14, further comprising:
  control circuitry,
    wherein two physical gradient axes from among the three orthogonal physical gradient axes are perpendicular to a longitudinal axis of the magnetic resonance imaging device and are disposed at angles of 45 degrees relative to the horizontal and the vertical direction, respectively, where the two radial through openings align, and
    wherein the control circuitry is configured to process acquired magnetic resonance data to a logical vertical gradient axis and a logical horizontal gradient axis.

* * * * *